United States Patent [19]

Turner et al.

[11] Patent Number: 4,968,343

[45] Date of Patent: Nov. 6, 1990

[54] FLUOROALKYL ANILIDE DERIVATIVES OF 2-(4-ARYLOXYPHENOXY)ALKANOIC OR ALKENOIC ACIDS AS SELECTIVE HERBICIDES

[75] Inventors: James A. Turner, Pittsburg, Calif.; Paul S. Zorner, Durham, N.C.

[73] Assignee: The Dow Chemical Company, Midland, Mich.

[21] Appl. No.: 27,586

[22] Filed: Mar. 18, 1987

Related U.S. Application Data

[63] Continuation-in-part of Ser. No. 776,714, Sep. 16, 1985, abandoned.

[51] Int. Cl.$^5$ .............................................. A01N 43/48
[52] U.S. Cl. ................................................. 71/92; 71/88; 71/90; 71/103; 71/105; 71/111; 71/118
[58] Field of Search ....................................... 71/92, 94

[56] References Cited

U.S. PATENT DOCUMENTS 4,130,413  12/1978  Handte et al. ........................ 71/90

FOREIGN PATENT DOCUMENTS 0042750  12/1981  European Pat. Off. .
82/00400  2/1982  PCT Int'l Appl. .

OTHER PUBLICATIONS

Mavor, General Biology, Third Ed., The Macmillan Company, New York, (1947), p. 355.
Kirk–Othmer, Encyclopedia of Chemical Technology, Third Ed., vol. 12, John Wiley & Sons, New York (1980), p. 297.

Primary Examiner—Glennon H. Hollrah
Assistant Examiner—Eric J. Kraus
Attorney, Agent, or Firm—S. Preston Jones; Ronald G. Brookens

[57]  ABSTRACT

The present invention is directed to the use of paratrifluoromethyl substituted aniline compounds, the optically active isomers of said compounds and compositions containing said compounds, in the selective kill and control of grassy weeds in the presence of corn plants.

9 Claims, No Drawings

FLUOROALKYL ANILIDE DERIVATIVES OF 2-(4-ARYLOXYPHENOXY)ALKANOIC OR ALKENOIC ACIDS AS SELECTIVE HERBICIDES

CROSS-REFERENCE TO RELATED APPLICATION

This is a continuation-in-part of U.S. application Ser. No. 776,714 filed Sept. 16, 1985 now abandoned.

BACKGROUND OF THE INVENTION

Fluoromethyl substituted anilide derivatives of 2-(4-aryloxyphenoxy)alkanoic or alkenoic acids and their general use as herbicides are known. For example, U.S. Pat. Nos. 3,954,442; 4,130,413; 4,134,753; 4,270,948 and 4,332,960; UK Patent Application Nos. 2,042,503A and 2,123,819A; European Patent Application No. 0042750; Canadian Pat. No. 1,137,484 and PCT Application No. WO 82/00400, all teach such anilide compounds, their preparation and herbicidal use.

SUMMARY OF THE INVENTION

The present invention is directed to the use of certain parasubstituted aniline compounds and the optically active isomers of said compounds as the active compounds in compositions used in the selective kill and control of grassy weeds in the presence of corn plants.

The active compounds employed in the present invention correspond to the formula

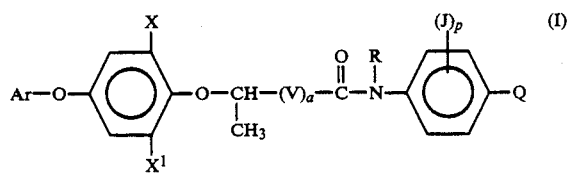

wherein Ar represents

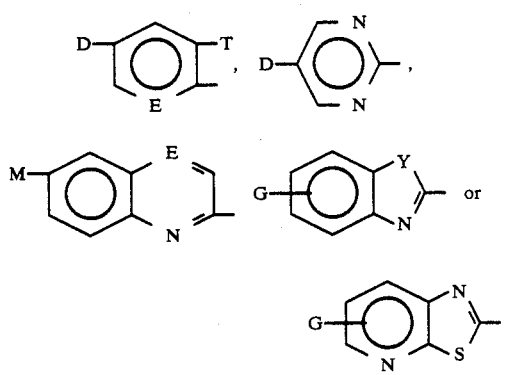

X and $X^1$ each independently represents —H, or —F;
Y represents oxygen or sulfur;
D represents —Br, —Cl, —I, or —CF$_3$;
E represents =N or =CH;
G represents at the 5 or 6-ring position, —CH$_3$, —CF$_3$, —Br, —Cl or —F;
M represents —CH$_3$, —CF$_3$, —Br, —Cl, —F or —I;
R represents —H, C$_1$-C$_4$ alkyl,

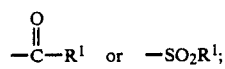

$R^1$ represents C$_1$-C$_4$ alkyl or phenyl substituted with from 0-3 C$_1$-C$_4$ alkyl groups;
J represents —Br, —Cl, —F, —I, —NO$_2$, —R$^2$, —CN, —OR$^2$, —NH$_2$, —NHR$^2$, —N(R$^2$)$_2$ or —COOR$^2$;
R$^2$ represents C$_1$-C$_4$ alkyl;
T represents —H, —Br, —Cl or —F;
Q represents —CF$_2$L;
L represents —H, —CF$_3$, —Br, —Cl or —F;
V represents —CH$_2$CH$_2$— or —CH=CH—;
a represents an integer of 0 or 1; and
p represents an integer of 0, 1 or 2.

The term "C$_1$-C$_4$ alkyl" as employed in the present specification and claims designates alkyl groups which can be straight or branched chain containing from 1 to 4 carbon atoms or cycloalkyl of 3 or 4 carbon atoms.

In the present invention, it is to be noted that all substituent groups are sterically compatible with each other. The term "sterically compatible" is employed to designate substituent groups which are not affected by steric hindrance as defined in "The Condensed Chemical Dictionary", 7th edition, Reinhold Publishing Co., N.Y., page 893 (1966) which definition is as follows: "steric hindrance. A characteristic of molecular structure in which the molecules have a spatial arrangement of their atoms such that a given reaction with another molecule is prevented or rewarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd edition, McGraw-Hill Book Company, N.Y., page 215 (1964).

The active compounds of the present invention contain the optically active center

and can exist in optically active stereoisomeric forms such as the R and S enantiomeric forms. The use of the various mixtures and racemates of the above isomers are within the scope of the present invention. Additionally, the R enantiomer of such compounds have been found to be more active biologically than the S enantiomer and may be used whenever the greater activity justifies the extra expenses for the use of this isomer.

A general discussion of the isomer activity difference phenomenon can be found in A. Albert, Selective Toxicity, 4th ed., Met Luen & Co., Ltd., London, 1968, pp. 387-390 and more particular discussions in A. Fredga and B. Åberg, "Stereoisomerism in plant growth regulators of the auxin type", Ann. Rev. Plant Physiology 16:53-72, 1965 and in E. J. Lien, J. F. R. DeMiranda and E. J. Airens, "Quantitative structure-activity correlation of optical isomers", Molecular Pharmacology 12:598-604, 1976.

The active compounds of the present invention are generally solid materials having low mammalian toxicity. The compounds are substantially insoluble in water and moderately soluble in common organic solvents.

The active compounds of the present invention, hereinafter referred to as "active compounds" or "active ingredients", have been found to be useful as herbicides for the postemergent kill and control of undesirable vegetation, for example, grassy or graminaceous weeds in the presence of corn plants.

The term "herbicide" is used herein to mean an active ingredient which controls or adversely modifies the growth of plants because of phytotoxic or other effects substantial enough to seriously retard the growth of the plant or further to damage the plant sufficiently to kill the plant.

The terms "growth controlling" or "herbicidally-effective" amount are employed to designate an amount of active ingredient which causes a modifying effect and includes deviations from natural development, killing, regulation, desiccation, retardation, and the like.

The term "plants" means established vegetation.

The terms "control" or "controlling" as it relates to plant growth has the same meaning as employed hereinabove for the term "herbicide".

Representative active compounds employed in the present invention are set forth below in Tables 1, 2, 3, 4 and 5.

TABLE 1

$$D\text{-}\underset{E}{\underset{|}{\bigcirc}}\text{-}T\text{-}O\text{-}\underset{X^1}{\underset{|}{\bigcirc}}\text{-}X\text{-}O\text{-}CH\text{-}(V)_a\text{-}\overset{O}{\overset{\|}{C}}\text{-}\overset{R}{\underset{|}{N}}\text{-}\underset{|}{\bigcirc}\text{-}Q \quad (J)_p$$
with $CH_3$ on the CH

| E | D | T | X | $X^1$ | $(V)_a$ | R | $(J)_p$ | Q |
|---|---|---|---|---|---|---|---|---|
| ≡N | —Br | —Cl | —H | —H | — | —H | —H | —$CF_3$ |
| ≡N | —Cl | —Cl | —H | —H | — | —$CH_3$ | —H | —$CF_3$ |
| ≡CH | —$CF_3$ | —F | —H | —H | — | —H | —H | —$CF_3$ |
| ≡N | —Br | —F | —H | —H | — | —H | —H | —$CF_3$ |
| ≡N | —I | —F | —F | —F | — | —$C_4H_9$ | 2-F | —$CF_3$ |
| ≡CH | —$CF_3$ | —F | —F | —H | — | —C(O)—$CH_3$ | —H | —$CF_3$ |
| ≡N | —I | —Cl | —F | —F | — | —H | 2-$CH_3$ | —$CF_2H$ |
| ≡CH | —$CF_3$ | —Cl | —H | —H | — | —H | —H | —$CF_3$ |
| ≡N | —$CF_3$ | —Cl | —H | —H | — | —H | —H | —$CF_3$ |
| ≡N | —Cl | —Cl | —H | —H | — | —$SO_2CH_3$ | —H | —$CF_3$ |
| ≡CH | —$CF_3$ | —Cl | —F | —F | — | —$SO_2C_4H_9$ | 2,3-$Cl_2$ | —$CF_3$ |
| ≡N | —$CF_3$ | —Br | —H | —H | — | —H | —H | —$CF_3$ |
| ≡N | —Cl | —F | —H | —H | — | —H | —H | —$CF_3$ |
| ≡N | —I | —F | —H | —H | — | —C(O)-phenyl | —H | —$CF_3$ |
| ≡N | —Cl | —Cl | —H | —H | —$CH_2CH_2$— | —H | —H | —$CF_3$ |
| ≡CH | —$CF_3$ | —Cl | —H | —H | —CHCH— | —H | —H | —$CF_3$ |
| ≡CH | —Br | —F | —H | —H | — | —$CH_3$ | 2-Cl | —$CF_3$ |
| ≡N | —I | —F | —F | —H | — | —C(O)—$CH_3$ | 2-$OCH_3$ | —$CF_3$ |
| ≡CH | —Cl | —Cl | —H | —H | — | —H | 2-Br | —$C_2F_5$ |
| ≡N | —$CF_3$ | —F | —H | —H | — | —H | —H | —$CF_3$ |
| ≡N | —Cl | —F | —H | —H | — | —H | —H | —$CF_3$ |
| ≡N | —Cl | —Cl | —H | —H | — | —H | —H | —$CF_2Cl$ |
| ≡CH | —Br | —F | —H | —H | — | —H | —H | —$CF_3$ |
| ≡CH | —Br | —F | —H | —H | — | —H | —H | —$C_2F_5$ |
| ≡CH | —Cl | —Cl | —H | —H | — | —H | —H | —$CF_2H$ |
| ≡CH | —Cl | —Cl | —H | —H | — | —H | —H | —$CF_3$ |

TABLE 2

$$D\text{-}\underset{N}{\overset{N}{\bigcirc}}\text{-}O\text{-}\underset{X^1}{\underset{|}{\bigcirc}}\text{-}X\text{-}O\text{-}CH\text{-}(V)_a\text{-}\overset{O}{\overset{\|}{C}}\text{-}\overset{R}{\underset{|}{N}}\text{-}\underset{|}{\bigcirc}\text{-}Q \quad (J)_p$$
with $CH_3$ on the CH

| D | X | $X^1$ | $(V)_a$ | R | $(J)_p$ | Q |
|---|---|---|---|---|---|---|
| —$CF_3$ | —H | —H | —CH:CH— | —H | —H | —$CF_3$ |
| —Cl | —H | —H | — | —H | —H | —$CF_3$ |
| —Cl | —H | —H | — | —H | —H | —$CF_3$ |
| —I | —F | —F | — | —H | —H | —$CF_3$ |
| —Br | —H | —H | — | —$CH_3$ | 2-Cl | —$CF_3$ |
| —$CF_3$ | —F | —F | — | —$CH_3$ | 3-Cl | —$CF_3$ |

TABLE 2-continued

Structure: D-pyrimidine-O-phenyl(X,X¹)-O-CH(CH₃)-(V)ₐ-C(=O)-N(R)-phenyl(J)ₚ-Q

| D | X | X¹ | (V)ₐ | R | (J)ₚ | Q |
|---|---|---|---|---|---|---|
| —CF₃ | —H | —H | — | —C(=O)CH₃ | 2-Cl | —CF₃ |
| —CF₃ | —H | —H | — | —C(=O)-phenyl | 3-NO₂ | —CF₃ |
| —Cl | —H | —H | — | —H | —H | —C₄H₉ |
| —Cl | —F | —F | — | —H | 2-CN | —CF₃ |
| —I | —H | —H | —CH₂CH₂— | —C(=O)—C₄H₉ | 3-OC₄H₉ | —CF₃ |
| —Br | —F | —F | — | —SO₂CH₃ | 2,3-Cl₂ | —CF₃ |
| —Br | —H | —H | — | —H | 3-Br | —CF₃ |
| —Cl | —F | —H | — | —H | 3-CH₃ | —CF₃ |
| —I | —H | —H | — | —CH₃ | —NO₂ | —CF₃ |
| —Cl | —H | —H | — | —H | —H | —CF₂H |
| —Cl | —H | —H | — | —H | —Cl | —CF₂Cl |
| —Cl | —H | —H | — | —H | 3,5-Cl₂ | —CF₂Br |

TABLE 3

Structure: Q-phenyl(E,N)-O-phenyl(X,X¹)-O-CH(CH₃)-(V)ₐ-C(=O)-N(R)-phenyl(J)ₚ-Q

| E | Q | X | X¹ | (V)ₐ | R | (J)ₚ | Q |
|---|---|---|---|---|---|---|---|
| ≡CH | —F | —H | —H | — | —H | —H | —CF₃ |
| ≡N | —Cl | —F | —H | — | —H | —H | —CF₃ |
| ≡N | —Cl₃ | —F | —H | —CH₂CH₂— | —H | —H | —CF₃ |
| ≡N | —CH₃ | —F | —H | — | —H | —H | —CF₃ |
| ≡CH | —Br | —H | —H | —CH:CH— | —H | —H | —CF₃ |
| ≡N | —Br | —F | —F | — | —H | —H | —CF₃ |
| ≡N | —I | —H | —H | — | —H | —NO₂ | —CF₃ |
| ≡N | —Cl | —H | —H | — | —H | —H | —CF₃ |
| ≡N | —Cl | —H | —H | — | —H | —Cl | —CF₃ |
| ≡N | —F | —H | —H | — | —C₂H₅ | 2,3-Cl₂ | —CF₃ |
| ≡N | —Br | —H | —H | — | —C(=O)—C₄H₉ | 2-CH₃ | —CF₃ |
| ≡CH | —Cl | —H | —H | — | —H | 3-Cl | —CF₂Cl |
| ≡CH | —CF₃ | —H | —H | — | —H | 2-F | —CF₃ |
| ≡N | —CF₃ | —H | —H | — | —SO₂C₄H₉ | —H | —CF₃ |
| ≡N | —CH₃ | —H | —H | — | —C(=O)CH₃ | —H | —CF₃ |
| ≡N | —Cl | —H | —H | — | —CH₃ | —H | —CF₂H |
| ≡N | —F | —H | —H | — | —H | —H | —CF₃ |
| ≡N | —Cl | —H | —H | — | —C₄H₉ | —H | —CF₃ |
| ≡CH | —Cl | —F | —F | — | —H | —H | —CF₃ |
| ≡CH | —Cl | —H | —F | — | —H | 2-NH₂ | —CF₃ |
| ≡N | —CF₃ | —H | —H | — | —SO₂C₄H₉ | 3,5-Cl₂ | —CF₃ |
| ≡N | —F | —F | —F | — | —H | 2,3-Cl₂ | —CF₃ |
| ≡N | —F | —H | —H | — | —H | 2,3-Cl₂ | —CF₃ |
| ≡N | —Cl | —H | —H | — | —SO₂phenyl | 2-Cl | —CF₃ |
| ≡CH | —Cl | —H | —H | — | —H | —H | —CF₃ |
| ≡CH | —Br | —H | —H | — | —H | 2-Br | —CF₂Br |

TABLE 4

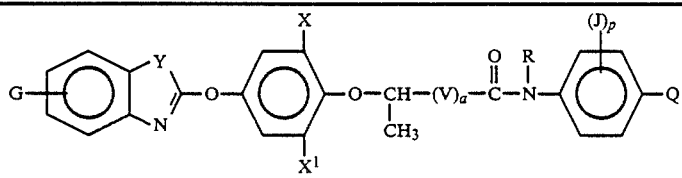

| G | Y | X | X¹ | (V)$_a$ | R | (J)$_p$ | Q |
|---|---|---|---|---|---|---|---|
| -6-CF$_3$ | S | —F | —F | — | —C(O)CH$_3$ | —H | —CF$_3$ |
| -5-CF$_3$ | O | —H | —H | —CH$_2$CH$_2$— | —H | 2-F | —CF$_3$ |
| -5-Br | S | —H | —H | —CH:CH— | —CH$_3$ | —H | —CF$_3$ |
| -6-Cl | S | —H | —H | — | —C$_3$H$_7$ | —Cl | —CF$_3$ |
| -5-Br | O | —H | —H | — | —H | —Cl | —CF$_3$ |
| -6-Br | S | —F | —H | — | —SO$_2$CH$_3$ | 2,3-Cl$_2$ | —CF$_3$ |
| -6-Cl | O | —H | —H | — | —H | 2-Cl | —CF$_3$ |
| -5-CH$_3$ | O | —H | —H | — | —H | —H | —CF$_3$ |
| -5-CF$_3$ | O | —H | —H | — | —H | —H | —CF$_3$ |
| -5-CF$_3$ | O | —F | —F | — | —H | 3-Cl | —CF$_3$ |
| -6-Cl | O | —H | —H | — | —H | 3,5-Br$_2$ | —CF$_3$ |
| -6-Cl | S | —H | —H | — | —C(O)C$_2$H$_5$ | 2-Cl | —CF$_3$ |
| -6-Cl | S | —H | —H | — | —CH$_3$ | 2-Cl | —CF$_2$H |
| -6-CH$_3$ | S | —H | —H | — | —H | —H | —CF$_3$ |
| -6-Cl | O | —F | —H | — | —H | —H | —CF$_3$ |
| -6-F | S | —H | —H | — | —H | —H | —CF$_3$ |
| -6-Br | O | —H | —H | — | —SO$_2$CH$_3$ | —H | —CF$_3$ |
| -6-F | O | —H | —H | — | —H | —H | —CF$_3$ |
| -6-Cl | O | —H | —H | — | —H | —H | —CF$_3$ |

TABLE 5

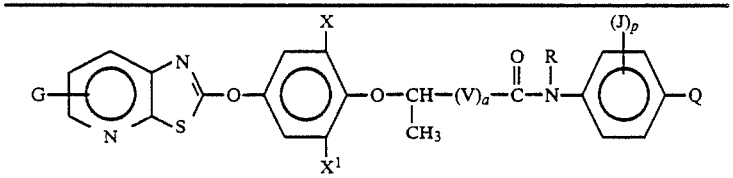

| G | X | X¹ | (V)$_a$ | R | (J)$_p$ | Q |
|---|---|---|---|---|---|---|
| -6-CF$_3$ | —H | —H | — | —H | —H | —CF$_3$ |
| -6-F | —H | —H | — | —H | —H | —CF$_3$ |
| -5-CF$_3$ | —F | —F | — | —H | —H | —CF$_3$ |
| -5-Cl | —H | —H | — | —C$_2$H$_5$ | 2-Cl | —CF$_3$ |
| -5-Br | —F | —H | — | —H | 3-Cl | —CF$_3$ |
| -5-Br | —F | —F | — | —H | —H | —CF$_3$ |
| -6-Br | —H | —H | — | —SO$_2$CH$_3$ | —H | —CF$_3$ |
| -6-Cl | —H | —H | — | —H | —H | —CF$_3$ |
| -6-Cl | —H | —H | — | —H | 2-Cl | —CF$_3$ |
| -6-Cl | —H | —H | — | —C$_4$H$_9$ | —H | —CF$_3$ |
| -5-CF$_3$ | —F | —H | — | —CH$_3$ | —H | —CF$_3$ |
| -5-CF$_3$ | —F | —F | — | —H | —H | —CF$_3$ |
| -6-Br | —H | —H | —CH:CH— | —H | —H | —CF$_3$ |
| -5-F | —F | —F | — | —H | —H | —CF$_3$ |
| -5-F | —F | —H | — | —H | —H | —CF$_2$Cl |
| -6-F | —F | —F | — | —H | —H | —CF$_2$H |
| -6-CF$_3$ | —H | —H | — | —H | —H | —CF$_2$Br |

The compounds of the present invention are all known and can be prepared employing the procedures taught in U.S. Pat. Nos. 3,954,442; 4,130,413; 4,134,753; 4,270,948 and 4,332,960; British Patent Application Nos. 2,042,503A and 2,123,819A; European Patent Application No. 0042750; Canadian Pat. No. 1,137,484 and PCT Application No. WO 82/00400. The preparative teachings of these above cited patents are incorporated herein by reference.

The active compounds of the present invention, as indicated, can be prepared employing a variety of preparative procedures. In one such procedure, substantially equimolar amounts of an appropriate acid halide corresponding to the formula

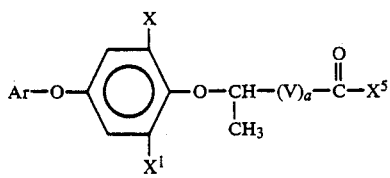

(II)

wherein Ar, X, X¹ and (V)$_a$ are as hereinbefore defined and X⁵ represents —Br, —Cl or —F with an aniline corresponding to the formula

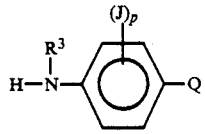

(III)

wherein (J)$_p$ and Q are as hereinbefore defined and R³ is —H or C$_1$–C$_4$ alkyl in the presence of an inert solvent and a hydrogen halide absorber (acid scavenger).

The reaction is generally conducted at temperatures of from about 0° C. up to the reflux temperature of the mixture. Normally temperatures of from about 0° to about 100° C. are all that's necessary.

While not normally necessary, a catalyst can be employed, if desired. Representative catalysts include, for example, 4-dimethylaminopyridine and 1,4-diazabicyclo-2,2,2-octane.

Representative inert solvents for this reaction include, for example, chlorinated hydrocarbons (for example, methylene chloride), ether, toluene, hexane, acetonitrile and the like.

Representative hydrogen halide absorbers include tertiary amines, alkali metal hydroxides and alkali metal carbonates. Alternatively, it has also been found that the addition of a molar excess of the amine reactant can function as the hydrogen halide absorber. Additionally, when pyridine is employed as the solvent, it can also function as the hydrogen halide absorber.

In an alternative procedure, the active compounds of the present invention can be prepared by the reaction of substantially equimolar amounts of an appropriate Ar compound corresponding to the formula Ar—X⁶ (IV)

wherein Ar is as hereinbefore defined and X⁶ represents —Br, —Cl, —F or —SO$_2$R¹ and an appropriate amide corresponding to the formula

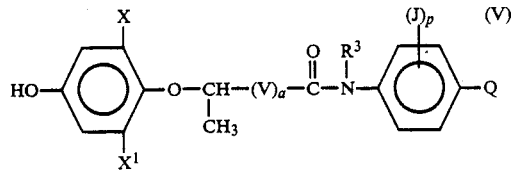

(V)

wherein R³, X, X¹, (V)$_a$, (J)$_p$ and Q are as hereinbefore defined. In carrying out this reaction, the reactants and a strong base such as an anhydrous alkali metal hydride, alkoxide, hydroxide or carbonate are mixed together in a dipolar, aprotic solvent such as, for example, dimethylformamide (DMF), acetone, methyl ethyl ketone, acetonitrile, dimethylsulfoxide (DMSO), sulfolane, N-methylpyrrolidone or the like. The reaction is advantageously carried out at elevated temperatures of from about 50° to 120° C.

In another procedure, the active compounds of the present invention can be prepared by the reaction of substantially equimolar amounts of an appropriate acid corresponding to the formula

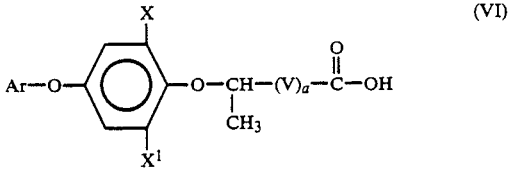

(VI)

wherein Ar, X, X¹ and (V)$_a$ are as hereinbefore defined with an aniline corresponding to Formula III in the presence of an inert reaction medium or solvent and a dehydrating agent such as, for example, dicyclohexylcarbodiimide (DCC) or a mixture of triphenyl phosphine and carbon tetrachloride. The reaction is usually conducted at temperatures of from about 0° C. to about 100° C. Other acceptable dehydrating agents and examples of their use in preparing amides from carboxylic acids and amines are included in Chapter 6, section 77 of the "Compendium of Organic Synthetic Methods", a 5 volume set, John Wiley & Sons; Wiley-Interscience Division, New York, N.Y. The above-indicated preparative teachings are incorporated herein by reference.

In another procedure, the active compounds of the present invention can be prepared by the reaction of substantially equimolar amounts of an appropriate acid ester corresponding to the formula

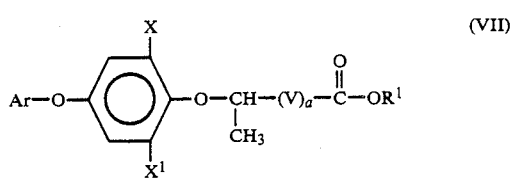

(VII)

wherein Ar, R¹, X, X¹ and (V)$_a$ are as hereinbefore defined, with an aniline corresponding to Formula III. This reaction is usually conducted in the presence of a polar solvent and at elevated temperatures of from about 50° C. to about 150° C. Depending on the specific reactants employed, a catalyst can be employed, if desired. Representative catalysts include those conventionally employed for ester-amide interchange.

The specific reaction times employed in the hereinabove and hereinafter set forth preparative procedures vary considerably and are dependent upon factors such as the solvent, base, catalyst, if employed, reaction temperature and the reactivity of the specific reactants employed. The reactions are for the most part complete in a period of from about 30 minutes to about 12 hours or more.

The active compounds of the present invention wherein Ar is an N-Oxide of a quinolinyl or quinoxalinyl moiety can be easily prepared by well known conventional oxidation procedures. In one such procedure, a quinolinyl or quinoxalinyl compound is treated with 30 percent hydrogen peroxide in acetic acid or trifluoroacetic acid.

The active compounds of the present invention wherein R is

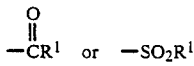

can be prepared by the reaction of substantially equimolar amounts of a compound of Formula I wherein R is hydrogen with a strong base such as one of those set forth hereinbefore followed by the direct treatment of the resulting material without separation, with an acid halide of the formula

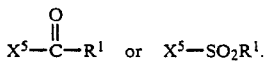

Such general reaction procedures can be found in European Patent Application No. 0042750; Japanese Patent Application No. 77,125,626 (Chemical Abstracts 88:190595K) and U.S. Pat. Nos. 4,246,419 and 4,270,948.

The desired product can be separated from the reaction product of the above preparative procedures employing conventional separatory procedures known to those skilled in the art including steps of solvent extraction, filtration, water washing, column chromatography, neutralization, acidification, crystallization and distillation.

The preparation of the optical isomer forms of the active compounds of the present invention follow conventional procedures employed to prepare related compounds. Such procedures include those taught in U.S. patent application Ser. No. 30,274 (filed July 14, 1983), European Patent Application Nos. 2800, 3890 and 6608; German OLS No. 29 49 728 and U.K. Patent Application GB No. 2,042,503A. The teachings of these applications are incorporated herein by reference thereto.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an excess of one reactant, the use of a catalyst, the use of high temperature and/or pressure equipment, high speed mixing and other such conventional changes are within the scope of this invention.

The following examples illustrate the present invention and the manner in which it can be practiced but as such, are not to be construed as limitations upon the overall scope of the same.

EXAMPLE I 2-(4-((3-Chloro-5-(trifluoromethyl)-2-pyridinyl)oxy)-phenoxy)-N-(4-(trifluoromethyl)phenyl)propanamide

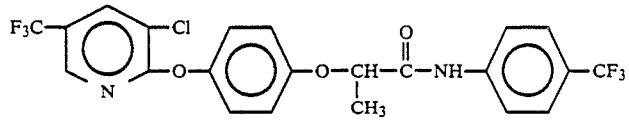

Step A: A mixture of 7.0 grams (g) (19.4 millimoles (mmol) of 2-(4-((3-chloro-5-(trifluoromethyl)-2-pyridinyl)oxy)phenoxy)propionic acid and 50 ml of thionyl chloride were warmed at reflux for 45 minutes. The excess thionyl chloride was then removed by vacuum distillation and the resulting acid chloride residue product was used without further purification.

Step B: A solution of the 2-(4-((3-chloro-5-(trifluoromethyl)-2-pyridinyl)oxy)phenoxy)propionyl chloride (prepared in Step A) in 50 ml of acetonitrile was added to a mixture of 3.82 g (19.4 mmol) of 4-aminobenzotrifluoride, hydrochloride and 4.90 g (48.4 mmol) of triethylamine in 25 ml of acetonitrile. The reaction mixture was warmed at reflux for 4.0 hours and then poured over crushed ice. The resulting precipitate was collected by filtration and dried. The residual solid was recrystallized from methylcyclohexane to give 9.1 g (93 percent of theoretical) of the above-named product as a tan solid which melted at 140°–143° C. The structure of the product was confirmed by its IR and NMR spectrum. (Compound 1)

Analysis: Calc. for $C_{22}H_{15}ClF_6N_2O_3$: C, 52.34; H, 3.00; N, 5.55; Found: C, 52.17; H, 3.00; N, 5.62.

EXAMPLE II 2-(4-((3-Fluoro-5-(trifluoromethyl)-2-pyridinyl)oxy)-phenoxy)-N-(4-(trifluoromethyl)phenyl)propanamide

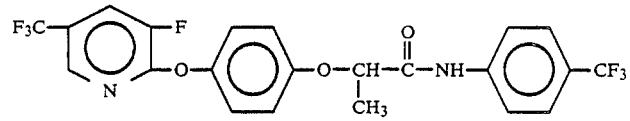

Step A: A mixture of 2.25 g (6.5 mmol) of 2-(4-((3-fluoro-5-(trifluoromethyl)-2-pyridinyl)oxy)phenoxy)-propanoic acid, 12 ml of thionyl chloride and 3 drops of DMF were warmed at reflux for a period of 1.5 hours. The excess thionyl chloride was removed by distillation and the residual acid chloride was used without further purification.

Step B: A solution of the 2-(4-((3-chloro-5-(trifluoromethyl)-2-pyridinyl)oxy)phenoxy)propionyl chloride prepared in Step A in 10 ml of methylene chloride was added slowly to an ice-cooled solution of 1.54 g (7.8 mmol) of 4-aminobenzotrifluoride, hydrochloride and 1.64 g (16 mmol) of triethylamine and 40 ml of methylene chloride. The reaction mixture was stirred at room temperature for 2 hours and then poured into a dilute aqueous HCl solution. The organic layer was separated, washed with a saturated aqueous $NaHCO_3$ solution, dried over $Na_2SO_4$ and evaporated to dryness. The residual solid material was recrystallized from methylcyclohexane to give 1.9 g (60 percent of theoretical) of the above-named product as a colorless solid material which melted at 127°–128.5° C. The structure of the product was confirmed by its IR and NMR spectrum (Compound 2).

Analysis: Calc. for $C_{22}H_{15}F_7N_2O_3$: C, 54.10; H, 3.10; N, 5.74, Found: C, 54.00; H, 3.07; N, 5.76.

EXAMPLE III 2-(4-((6-Fluoro-2-quinolinyl)oxy)phenoxy)-N-(4-(trifluoromethyl)phenyl)propanamide

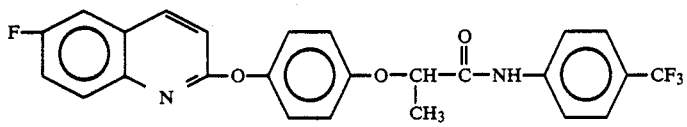

A solution of 5 mmol of 2-(4-((6-fluoro-2-quinolinyl)oxy)phenoxy)propionyl chloride, prepared using substantially the procedure of Step A of Example 1 from the corresponding acid in 5 milliliters (ml) of methylene chloride, was slowly added to an ice-cooled solution comprising 0.89 grams (g) (5.5 mmol) of 4-aminobenzotrifluoride and 0.61 g (6 mmol) of triethylamine in 30 ml of methylene chloride. The reaction mixture was stirred at 0° C. for 30 minutes then at room temperature for 2 hours. The mixture was poured into a dilute aqueous HCl solution. The organic layer was separated, washed with water, then washed with a saturated aqueous NaHCO₃ solution, dried over MgSO₄ and evaporated to dryness. The residual solid was taken up in boiling methylcyclohexane, filtered and filtrate allowed to cool to give 1.68 g (71 percent of theoretical) of the above-named product as colorless crystals. The product melted at 153°–155° C. and its structure was confirmed by its infrared (IR) and its nuclear magnetic resonance (NMR) spectrum. (Compound 3)

Analysis: Calc. for $C_{25}H_{18}F_4N_2O_3$: C, 63.83; H, 3.86; N, 5.96; Found: C, 63.60; H, 3.80; N, 5.78.

EXAMPLE IV 2-(4-((6-Fluoro-2-quinoxalinyl)oxy)phenoxy)-N-(4-(trifluoromethyl)phenyl)propanamide

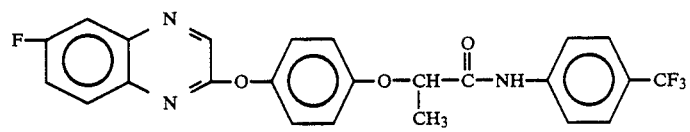

Step A: A mixture of 1.38 g (4.2 mmol) of 2-(4-((6-fluoro-2-quinoxalinyl)oxy)phenoxy)propanoic acid and 10 ml of thionyl chloride were warmed at reflux for 2 hours. The excess thionyl chloride was removed by vacuum distillation and the resulting acid chloride product was used without further purification.

Step B: A solution of the acid chloride prepared in Step A in 10 ml of methylene chloride was added dropwise to a ice cooled solution of 0.74 g (4.6 mmol) of 4-aminobenzotrifluoride and 0.64 g (6.3 mmol) of triethylamine in 30 ml of methylene chloride. The reaction mixture was allowed to slowly warm to room temperature and then poured into ice water. The organic layer was separated, washed with a saturated aqueous NaHCO₃ solution, dried over MgSO₄ and evaporated to dryness. The residual solid was recrystallized from methylcyclohexane to give 1.55 g (78 percent of theoretical) of the above-named product. The product was colorless crystals and melted at 172°–174° C. and its structure was confirmed by its IR and NMR spectrum. A second recrystallization from methylcyclohexane gave an analytical sample melting at 175°–177° C. (Compound 4)

Analysis: Calc. for $C_{24}H_{17}F_4N_3O_3$: C, 61.15; H, 3.64; N, 8.91; Found: C, 60.73; H, 3.62; N, 8.72.

EXAMPLE V 2-(4-((6-Chloro-2-quinoxalinyl)oxy)phenoxy)-N-(4-(trifluoromethyl)phenyl)propanamide

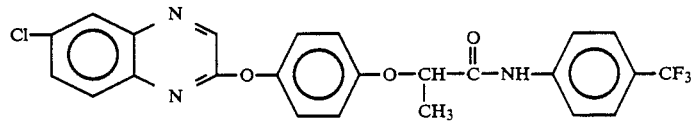

A solution of 7.25 mmol of 2-(4-((6-chloro-2-quinoxalinyl)oxy)phenoxy)propionyl chloride, prepared using substantially the procedure of Step A of Example 1 from the corresponding acid, in 20 ml of acetonitrile was added to solution of 1.43 g (7.25 mmol) of 4-aminobenzotrifluoride, hydrochloride and 1.83 g (18.1 mmol) of triethylamine in 10 ml of acetonitrile. The reaction mixture was warmed at reflux for a period of 4 hours and then poured over crushed ice. The resulting precipitate was collected by filtration and then recrystallized from acetonitrile to give 2.40 g (68 percent of theoretical) of the above-named product as a tan solid which melted at 176°–178° C. The structure of the product was confirmed by its IR and NMR spectrum. (Compound 5)

Analysis: Calc. for $C_{24}H_{17}ClF_3N_3O_3$: C, 59.09; H, 3.51; N, 8.61; Found: C, 58.96; H, 3.63; 8.69.

EXAMPLE VI 2-(4-((6-Chloro-2-quinolinyl)oxy)phenoxy)-N-(4-(tri-fluoromethyl)phenyl)propanamide

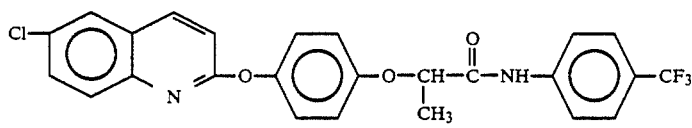

A solution of 5 mmol of 2-(4-((6-chloro-2-quinolinyl-)oxy)phenoxy)propionyl chloride, prepared as in Step A of Example 1 employing the corresponding acid, in 10 ml of methylene chloride was added dropwise to an ice-cooled solution of 1.09 g (5.5 mmol) of 4-aminobenzotrifluoride, hydrochloride, 1.21 g (12.0 mmol) of triethylamine and 50 ml of methylene chloride. The reaction mixture was stirred at room temperature for 3 hours and then poured into a dilute aqueous HCl solution. The organic layer was separated, washed with a saturated aqueous NaHCO$_3$ solution, dried over MgSO$_4$ and evaporated to dryness. The residual solid was recrystallized from methylcyclohexane to give 1.79 g (74 percent of theoretical) of the desired product as colorless crystals melting at 142°–146° C. The structure of the compound was confirmed by its IR and NMR spectrum. (Compound 6). The carbon, hydrogen and nitrogen contents were determined to be as follows:

Analysis: Calc. for $C_{25}H_{18}ClF_3N_2O_3$: C, 61.67; H, 3.73; N, 5.76; Found: C, 61.71; H, 3.77; N, 5.90.

Preparation of Starting Materials

The carboxylic acids, acid halides and esters employed herein as starting materials and which correspond to the formula

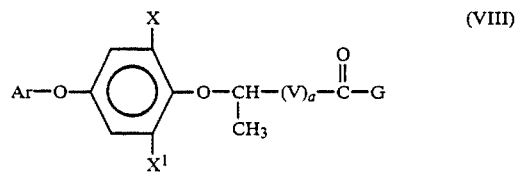

(VIII)

wherein G represents —OH, —X$^5$ or —OR$^1$ and Ar, X, X$^1$, X$^5$, (V)$_a$ and R$^1$ are as hereinbefore set forth are for the most part known compounds and various compounds corresponding to Formula VIII and their preparation can be found in the known art including Canadian Patent No. 1,179,350; European Patent Application Nos. 23,785; 47,972; 50,019; British Pat. No. 2,042,539; Japanese Kokai Nos. 55-111467; 55-120565 and 55-154936; U.S. Pat. Nos. 4,236,912; 4,325,729 and 4,444,584; and U.S. patent application Ser. No. 550,328, filed Nov. 10, 1983. In addition, compounds of Formula VIII not specifically taught can be prepared by procedures analogous to those of the above references.

The aromatic/heterocyclic halides employed as starting materials and which correspond to the formula Ar—X$^6$  (IV)

wherein Ar and X$^6$ are as hereinbefore defined, are all known and/or commercially produced compounds and for the most part are taught in the above-listed applications and/or patents which teach preparing compounds of Formula VIII.

The aniline compounds employed as starting materials and which correspond to the formula (III)

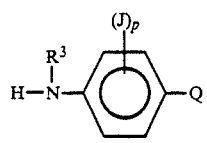

wherein R$^3$, (J)$_p$, A and Q are as hereinbefore defined are for the most part known compounds as shown and/or taught in U.S. Pat. Nos. 3,954,442; 4,130,413; 4,134,753; 4,270,948 and 4,332,960. Many of the compounds are articles of commerce and those compounds not known can be prepared by the processes used to prepare the known compounds employing the appropriate starting materials.

The substituted amides employed as starting materials and which correspond to the formula

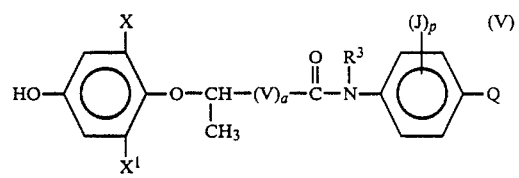

(V)

wherein X, X$^1$, (V)$_a$, R$^3$, (J)$_p$ and Q are as hereinbefore defined, can be prepared by the reaction of substantially equimolar amounts of an appropriate ester corresponding to the formula

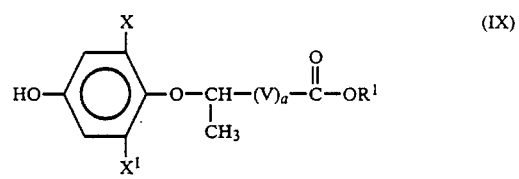

(IX)

wherein X, X$^1$, (V)$_a$ and R$^1$ are as hereinabove defined (taught in the references for preparing compounds of Formula VII) with an appropriate aniline compound of Formula III, in an inert, non-acidic polar solvent. In carrying out this reaction, the reactants and the solvent are mixed together and heated at a temperature of from about 50° C. up to the refluxing temperature of the mixture. After the completion of the reaction, the product is recovered after the removal of the solvent and any excess amine; in most cases, evaporation procedures are sufficient.

In an alternative procedure for preparing the amide of Formula (V), substantially equimolar amounts of an appropriate hydroquinone which contains a protecting group (W) and which corresponds to the formula

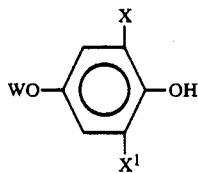

(X)

wherein X and X¹ are as hereinbefore defined and W represents a protecting group are reacted with a substituted amide corresponding to the formula

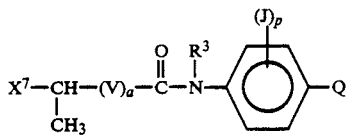

(XI)

wherein $(V)_a$, $R^3$, $(J)_p$ and Q are as hereinbefore defined and $X^7$ is —Br, —Cl, —OSO₂R¹.

Protecting groups and their use in reactions involving hydroquinone compounds are well known to those skilled in the art. Such usage is taught in "Protective Groups in Organic Synthesis" by T. W. Greene; Chapter 3 *Protection For Phenols and Catechols*; John Wiley & Sons, New York, N.Y.; (1981), which is being incorporated herein by reference thereto. The specific protecting group employed is not critical, any of the conventionally employed protecting groups can be employed herein as long as this group is not reactive with the amide. Representative groups include —CH₃, —CH₂OCH₃, —CH₂OCH₂CH₂OCH₃ and the like.

In carrying out this reaction, the protected hydroquinone and the amide are mixed together in an inert dipolar, aprotic solvent such as, for example, acetonitrile, acetone, methyl ethyl ketone, DMF or DMSO. In addition, a strong base such as an anhydrous alkali metal carbonate, hydroxide or hydride is present to deprotonate the hydroquinone. The reaction is conducted at a temperature of from about 25° C. up to the reflux temperature of the mixture. At the completion of this reaction, the product is usually recovered employing conventional steps including extraction, water and alkali washing and distillation.

The above product is then deprotected employing a variety of techniques depending upon the nature of the protecting group. The above cited Greene reference describes such techniques. As one example, the above product where W is —CH₂OCH₃ is mixed with an alcoholic solvent and a catalytic amount of a strong acid and refluxed for up to 24 hours to convert the product to the desired hydroxy compound. Representative acids include p-toluenesulfonic acid, and the like. The product is thereafter recovered employing conventional procedures of solvent evaporation, solvent extraction and the like.

In a variation of the above procedure, the amide of Formula V can be prepared directly from the unprotected hydroquinone by the slow addition of the amide of Formula XIV to a mixture containing one of the above solvents, strong base and an excess of the hydroquinone.

EXAMPLE VII 4-(Methoxymethoxy)phenol

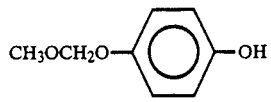

A mixture of 55.0 g (0.5 mol) of hydroquinone, 500 milligrams (mg) of p-toluenesulfonic acid monohydrate, 200 ml of dimethoxymethane and 1000 ml of methylene chloride were warmed to a vigorous reflux. The distillate was passed through a soxhlet extractor which had been charged with approximately 300 g of 4 Å molecular sieves. After 18 hours an additional 500 mg of p-toluenesulfonic acid monohydrate was added and refluxing continued for an additional 24 hours. The reaction mixture was then cooled and 20 ml of triethylamine was added and the mixture filtered. The filtrates were evaporated to near dryness and the residue partitioned between ether and saturated aqueous sodium bicarbonate. The ether layer was extracted twice with portions of 5 percent aqueous sodium hydroxide. The combined aqueous layers were washed with ether and then made acidic with acetic acid. The aqueous mixture was extracted twice with portions of ether and the combined ether layers washed with saturated aqueous sodium bicarbonate, dried over MgSO₄ and evaporated to dryness. The residue was distilled in a Kugelrohr apparatus at 120° C. and 0.07 mm Hg to give 37.1 g (48 percent of theoretical) of a reddish oil which was identified by NMR analysis as 4-(methoxymethoxy)phenol contaminated with a small amount of hydroquinone. The residual hydroquinone was removed by dissolving the oil in methylene chloride, washing the solution with water and then, after removal of the solvent, distilling the residue as before. This left 30.4 g of pure 4-(methoxymethoxy)phenol, as an oil.

The acid halides of the formula

and X⁵SO₂R¹ wherein X⁵ and R¹ are as hereinbefore defined and which are employed as starting materials are well known materials and their preparation is taught throughout the chemical literature. Many of the compounds are articles of commerce.

The compounds of the present invention have been found to be suitable for use in methods for the selective postemergent control of many annual and perennial grassy weeds in the presence of corn plants. It is to be noted that not all compounds will have the same effect on all weed plants. Some compounds will be more active in the control of one weed species than another.

For such uses, unmodified active ingredients of the present invention can be employed. However, the present invention also embraces the use of the active compounds in admixture with inert materials, known in the art as agricultural adjuvants and/or carriers, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally-effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as foxtail, barnyard grass, wild oats, Johnson grass and crabgrass while showing high selectivity to corn plants. These compounds are also uniquely effective in controlling perennial grassy weeds such as Johnson grass, quackgrass, and bermuda grass.

The exact amount of the active material to be applied is dependent not only on the specific active ingredient being applied, but also on the particular action desired, the weed plant species to be controlled and the stage of growth thereof as well as the part of the plant to be contacted with the toxic active ingredient. Thus, all of the active ingredients of the present invention and compositions containing the same may not be equally effective at similar concentrations or against the same weed plant species.

In the present postemergent operations, a dosage of about 0.01 to about 20 lbs/acre (0.056–22.4 kg/hectare) is generally applicable, although not all compounds are equally effective and some weeds are more difficult to control. Thus, a dosage rate in the range of about 0.05 to about 1.0 lb/acre (0.01–1.12 kg/hectare) is preferred in postemergent control of annual grassy weeds, while about 0.05 to about 5 lbs/acre (0.056–5.6 kg/hectare) is a preferred dosage range for the post-emergent control of perennial grassy weeds. In applications to corn plants a weed controlling but less than corn plant damaging amount of from about 0.005 to about 1.0 lb/acre (0.0056 to 1.12 kgs/hectare) is generally employed.

The following examples illustrate the effects of the compounds of this invention.

EXAMPLE VIII

Representative compositions of the present invention were evaluated to determine their effectiveness in postemergent operations.

Aqueous dispersions were prepared by admixing predetermined amounts of one of the hereinafter set forth compounds, dissolved in a predetermined amount of an inert solvent with a predetermined quantity of water and a predetermined amount of a surfactant to give aqueous dispersions of one of the compounds as the sole toxicant. The compounds tested were 2-(4-((3-chloro-5-(trifluoromethyl)-2-pyridinyl)oxy)phenoxy)-N-(4-(trifluoromethyl)phenyl)propanamide (Compound 1), 2-(4-((6-fluoro-2-quinoxalinyl)oxy)phenoxy)-N-(4-(trifluoromethyl)phenyl)propanamide (Compound 3), 2-(4-((6-chloro-2-quinolinyl)oxy)phenoxy)-N-(4-(trifluoromethyl)phenyl)propanamide (Compound 6) and 2-(4-((3-chloro-5-(trifluoromethyl)-2-pyridinyl)oxy)-2-fluorophenoxy)-N-(4-(trifluoromethyl)phenyl)-propanamide (Compound 7).

Plant seeds were planted in beds of good agricultural soil and grown in a greenhouse. After the plants had emerged and had grown to the four leaf stage, the plants were sprayed to runoff with one of the above-prepared compositions at a predetermined treating rate (in parts of the active compound per million parts of the ultimate composition (PPM)). Other beds of the plants were sprayed with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds and the percent post-emergent control are set forth below in Table 6.

TABLE 6

| Compound No. Tested | Treatment Rate in PPM | Percent Kill and Control of the Following Plant Species | | | | | |
|---|---|---|---|---|---|---|---|
| | | Corn | Barnyard Grass | Johnson Grass | Giant Foxtail | Green Foxtail | Yellow Foxtail |
| 1 | 250 | 10 | 100 | 100 | 100 | 100 | 100 |
| | 125(a) | 0 | 100 | 100 | 100 | 100 | 100 |
| | 62.5(a) | 0 | 80 | 100 | 100 | 100 | 100 |
| | 31.25 | 0 | 100 | 100 | 98 | 100 | 80 |
| | 15.75 | 0 | 20 | 98 | 95 | NT | NT |
| 3 | 500 | 0 | 100 | 100 | 100 | 100 | 100 |
| | 250 | 0 | 100 | 100 | 100 | 100 | 100 |
| | 125 | 0 | 100 | 100 | 100 | 100 | 100 |
| | 62.5 | 0 | 100 | 100 | 100 | NT | NT |
| 6 | 1000 | 5 | 50 | 100 | 100 | 100 | 100 |
| | 500 | 0 | 100 | 100 | 100 | 100 | 100 |

TABLE 6-continued

| Compound No. Tested | Treatment Rate in PPM | Percent Kill and Control of the Following Plant Species | | | | | |
|---|---|---|---|---|---|---|---|
| | | Corn | Barnyard Grass | Johnson Grass | Giant Foxtail | Green Foxtail | Yellow Foxtail |
| | 250 | 0 | 70 | 100 | 100 | 80 | 100 |
| 7 | 125 | 50 | 100 | 100 | 100 | 100 | 100 |
| | 62.50 | 30 | 100 | 100 | 100 | 100 | 95 |
| | 31.25 | 0 | 100 | 100 | 100 | 100 | 50 |

(a) unknown anomalies have been found at 125 ppm where one test has shown 10 percent kill and at 62.5 percent where one test showed a 50 percent kill.

What is claimed is:

1. A method for the selective postemergent control of grassy weed plants in the presence of corn plants which comprises applying to said plants a herbicidally effective amount of a composition comprising an agriculturally acceptable inert adjuvant in intimate admixture with, as the active material, a compound selected from the group consisting of 2-(4-((3-chloro-5-(trifluoromethyl)-2-pyridinyl)oxy)phenoxy)-N-(4-(trifluoromethyl)phenyl)propanamide, 2-(4-((3-chloro-5-(trifluoromethyl)-2-pyridinyl)oxy)-2-fluorophenoxy)-N-(4-(trifluoromethyl)phenylpropanamide, 2-(4-((6-chloro-2-quinolinyl)oxy)phenoxy)-N-(4-(trifluoromethyl)phenyl)propanamide and 2-(4-((6-fluoro-2-quinolinyl)oxy)phenoxy)-N-(4-(trifluoromethyl)phenyl)propanamide.

2. The method as defined in claim 1 wherein the active material is 2-(4-((3-chloro-5-(trifluoromethyl)-2-pyridinyl)oxy)phenoxy-N-(4-(trifluoromethyl)phenyl)propananamide.

3. The method as defined in claim 2 wherein the active material is in the R enantiomeric isomer form.

4. The method as defined in claim 1 wherein the active material is 2-(4-((3-chloro-5-(trifluoromethyl)-2-pyridinyl)oxy)-2-fluorophenoxy)-N-(4-(trifluoromethyl)phenyl)propanamide.

5. The method as defined in claim 4 wherein the active material is in the R enantiomeric isomer form.

6. The method as defined in claim 1 wherein the active material is 2-(4-((6-chloro-2-quinolinyl)oxy)phenoxy)-N-(4-(trifluoromethyl)phenyl)propanamide.

7. The method as defined in claim 6 wherein the active material is in the R enantiomeric isomer form.

8. The method as defined in claim 1 wherein the active material is 2-(4-((6-fluoro-2-quinolinyl)oxy)phenoxy)-N-(4-(trifluoromethyl)phenyl)propanamide.

9. The method as defined in claim 8 wherein the active material is in the R enantiomeric isomer form.

* * * * *